(12) United States Patent
Douglas

(10) Patent No.: US 6,187,031 B1
(45) Date of Patent: Feb. 13, 2001

(54) BIOMAGNETIC HOT AND COLD THERAPY PACK

(76) Inventor: Thomas E. Douglas, 100 Hillcrest St., Hot Springs, AR (US) 71901

( * ) Notice: Under 35 U.S.C. 154(b), the term of this patent shall be extended for 0 days.

(21) Appl. No.: 09/302,564

(22) Filed: Apr. 30, 1999

Related U.S. Application Data

(60) Provisional application No. 60/084,759, filed on May 8, 1998.

(51) Int. Cl.[7] ......................................................... A61F 7/00

(52) U.S. Cl. .............................. 607/112; 607/108; 600/15

(58) Field of Search ............................. 607/96, 104, 108, 607/109, 110, 111, 112; 600/15

(56) References Cited

U.S. PATENT DOCUMENTS

| 5,456,704 | * | 10/1995 | Kilcullen | 607/111 |
| 5,697,961 | * | 12/1997 | Kiamil | 607/108 |
| 5,888,185 | * | 3/1999 | Regan | 600/15 |
| 6,029,277 | * | 2/2000 | Picchione, II | 2/162 |

* cited by examiner

*Primary Examiner*—Linda C. M. Dvorak
*Assistant Examiner*—R. Kearney

(57) ABSTRACT

An improved magnetic hot or cold pack is provided having a water absorbent filler such as polyacrylamide and having at least one magnet and an accessory strap that allows the application of heat therapy, cold therapy, magnetic therapy or heat with magnet therapy or cold with magnet therapy. Also provided is a method of preparing a magnetic hot and cold therapy pack having a water absorbent filler such as polyacrylamide and at least one magnet and an accessory strap.

12 Claims, 3 Drawing Sheets

BIOMAGNETIC HOT AND COLD THERAPY PACK

This application is a continuation-in-part of Provisional Application No. 60/084,759 entitled "Biomagnetic Hot and Cold Therapy Pack" filed on May 8, 1998.

BACKGROUND OF THE INVENTION

The present invention relates to combining heat or cold therapy with magnet therapy. Application of heat therapy is a standard practice in medicine for the treatment of common ailments such as arthritis, bursitis, headache, back and neck pain, menstrual cramps, fibromyalgia and muscle soreness. Likewise cold therapy is a standard practice in medicine for the treatment of strains, sprains, headache and muscle spasms.

Medical professionals generally recommend cold therapy during the first 24 to 48 hours after the "acute" phase of an injury such as a strain or sprain. During this time, the blood vessels around the injured tissues open up, rushing blood, nutrients and fluids to the area to help the tissues heal. A problem is that the increased blood flow often causes the healthy tissues surrounding the injury to swell and become inflamed. If swelling and inflammation are not stopped or slowed, more extensive tissue damage may occur and the injury may take longer to heal. The additional fluids in the swollen tissues may press on nerves around the injury site, increasing pain. Cold therapy reduces swelling and inflammation in a number of ways: it lowers the skin temperature, which helps to constrict the blood vessels; it slows the metabolic rate of the injured tissues; and it slows the body's release of chemicals that dilate the blood vessels, further helping to reduce blood flow to the area. Cold therapy also numbs the injured area and reduces muscle spasms, both of which help to relieve pain.

Heat therapy is medically recommended for treatment to an injury after the swelling and inflammation subside, generally after the first 24–48 hours. Heat therapy increases skin temperature, causing blood vessels to dilate and increases blood flow to the area. The increased blood flow and nutrients help to nourish injured tissues. Heat also can relieve muscle spasms and pain triggered by loss of blood flow to the area, and increases the elasticity of the connective tissue of collagen, helping to decrease joint stiffness. Heat therapy is especially helpful in the treatment of tom muscles and tendons after the inflammation and swelling have gone down. Most medical textbooks recommend moist heat over dry heat due to moist heat's ability to penetrate deeper into the tissue thereby increasing blood flow, however it is not always convenient to use moist heat as it dampens clothing, bedding and furniture. See, Lehmann, *Therapeutic Heat and Cold*, pp. 440 (3rd edition, 1987).

Magnet therapy has been shown to assist in healing injuries. Researchers at Baylor University College of Medicine, Vanderbilt University Medical Center, Tufts University School of Medicine, Mount Sinai Medical Center and New York Medical College at Valhalla and others have published reports demonstrating the effectiveness of magnets in increasing blood flow, reducing pain from sports injuries, relieving pain from fibromyalgia, increasing collagen, reducing muscle spasms and decreasing joint stiffness. F. Wunsch-Binder of the Department of Radiology, University of Kiel Medical School, Germany, conducted a study called "The Influence of Static Magnetic Fields on Skin Temperature and Blood Flow in Man." He found that human skin undergoes temperature change within a static magnetic field. Temperature variations increased from 0.3 degrees centigrade to 5 degrees centigrade. It was assumed that the increase in temperature was caused by increase in blood flow.

William H. Phillpott, MD published his research on magnetic therapy in 1990, Phillpott and Taplin *Biomagnetic Handbook* (1990). His research indicates that magnets can reduce edema if the magnet is placed several inches to the side of an injury in order to pull fluids toward the positive field and away from the site of swelling. Phillpott suggests that magnets can increase cellular oxygenation and speed healing.

In a study conducted by Mount Sinai Medical Center, New York, to determine the effect of cell/tissue repair and regeneration, magnetic device patches were placed over wounds for a total of 48 hours. The results suggest that in approximately 60% of patients' pain, edema and discoloration were diminished, and in 75% of patients pain and edema disappeared.

The present invention allows the user to choose to apply moist heat or dry heat therapy, with or without magnet therapy, thus receiving the benefits of all three treatment modalities.

Multi-purpose moist heat-cold packs have been in use for several years. For example U.S. Pat No 5,447,531 to Wood and U.S. Pat No. 5,391,198 to Cheney illustrates such packs. However these type packs have several limitations. Both of these inventions use fabric for the envelope containing the superabsorbent polyacrylamide filler, however fabric is not a good conductor of cold, as the fabric acts as an insulation barrier between the filler and the skin, limiting appropriate cold application to approximately 10 minutes. Since most medical textbooks recommend cold therapy application of 48 degrees F. for 20 minutes these packs cannot deliver the medically recommended range of cold therapy. (Lehman, supra @ pp. 401–405) Also, the above referenced patents call for a water permeable membrane on both sides of the pack, which limits the pack to moist heat therapy. Also, Cheney teaches placing the pack in a refrigerator or freezer. As the interior filler contains no antifreeze properties, this pack would freeze solid if placed in the freezer, and thus not be pliable. Cheney teaches that the pack would be 21.4 degrees F. after 25 minutes out of a freezer. This pack and all other packs that require freezing would subject the patient to frostbite or skin damage, as 48 degrees F. as referenced by Lehman is the medically recommended range of cold therapy. Application of a pack such as Cheney teaches would could cause frostbite or skin damage to diabetics, children or individuals with poor circulation or decreased sensory perception. Also, a frozen pack such as Cheney teaches would be subject to causing a rip or tear in the fabric, due to the solid ice formation of the interior filler. Cheney further teaches the use of a synthetic fabric such as that sold under the trademark SONTARA by Dupont or other similar fabrics. Wood teaches a synthetic fabric such as NYLON coated with thin polyurethane. As SONTARA and NYLON are synthetic fabrics they and are both hydrophobic. Wood teaches the inclusion of cotton wicking material sewn into the pack to facilitate hydration of the polyacrylamide.

An advantage of the present invention is that the water permeable side of the pack utilizes the patented process (U.S. Pat. No. 5,855,623) of grafting of a hydrophilic molecule to the surface of the fiber which reduces the hydration time by approximately one half over Cheney and Wood. A hydrophilic fiber such as INTERA can be purchased from the INTERA Corporation, Chattanooga, TENN. The polyacrylamide-type packs taught by Wood and Cheney are also subject to mold, mildew and fungal and bacteria growth, as the surface material stays moist for days or weeks when not in use, providing an ideal environment for the growth of microorganisms. Another advantage of the INTERA fabric is that it reduces bacteria, mold, mildew and odors from forming on the pack, as the surface of the pack dries before microorganisms can replicate. Another advantage of using the INTERA fabric is that it is more soil resistant and easier to clean than SONTARA or NYLON. Another advantage over INTERA over fabrics taught in Wood and Cheney is that it improves the delivery of cold therapy due to the increased rate of evaporation of the water on the fabric surface, thus allowing evaporative cooling. Wood teaches the coating of the NYLON fabric with polyurethane to prevent the escape of polyacrylamide through the fabric weaves. Cheney does not refer to the escape of the polymer from the cavity. However, in actual use this is a major problem for both of these methods of construction. Over time and use the polyacrylamide breaks down into very small particles, which escape through the fabric, thus causing a slick and tacky surface. This is particularly true of the Cheney construction as no method of containment of the small particle polyacrylamide is provided. A polyether or ester foam laminated to the INTERA fabric has been found to improve the restriction of the seepage of the polyacrylamide molecules, due to the complex pore structure of the foam, and the ability of INTERA fabric to rapidly dehydrate any polyacrylamide which reaches the surface, thus eliminating any slick or tacky feel.

U.S. Pat. No. 5,179,944 issued to McSymytx teaches the application of moist heat, dry heat or cold to a patient, however this invention requires the user to place the pack in a separate cover for the delivery of dry heat, which is not necessary with the present invention. McSymytx also teaches filler material comprised of sand, which is expensive to ship and store, and would not easily conform to areas of the body such as wrists, knees or ankles. McSymytx also teaches cooling by freezer, thus bringing the application temperature below 32 degrees F. which is uncomfortable at best and could cause frostbite and skin damage the same as previously mentioned in Cheney. In addition McSymytx teaches a fabric exterior, which creates an insulation barrier between the skin and pack as Cheney and Wood, reducing the cold delivery time to about 10 minutes. Since the pack taught by McSymytx is conditioned by water and enclosed in fabric, it provides the same environment as Cheney and Wood for the growth of microorganisms on the surface of the pack.

U.S. Pat. No. 4,177,796 to Franco-Vila was granted teaching the incorporation of magnet and heat therapy in a vibrating device. The Franco-Vila patent is restricted to dry heat, vibration and magnetism. It also requires an AC power supply, and a teaches combination of electromagnets and permanent magnets. The present invention is an improvement over Franco-Vila in that it much less expensive to manufacture and therefore less expensive to the patient; is multi-purpose in that it allows application of any combination of magnets and dry heat, moist heat or cold therapy. The present invention is an improvement over Franco-Vila in that it does not require a power source for operation and allows application to areas of the body where a vibrating device is not appropriate such as the eyes. The present invention is a further improvement in that it allows several magnets to be grouped together for deeper penetration or spaced apart for a more wide spread therapeutic effect.

SUMMARY OF THE INVENTION

The present invention provides an improved multipurpose hot/cold therapy pack. More specifically, it is the object of the present invention to provide a method for application of heat therapy, cold therapy, magnet therapy or heat plus magnet therapy or cold plus magnet therapy to allow the combined therapeutic effect of magnet therapy with heat or cold therapy. An advantage of the present invention is that it provides a multi-purpose therapeutic pack.

Still further, an advantage of the present invention is that it allows the application of moist heat therapy;

A further advantage of the present invention is that it allows the application of dry heat therapy;

A further advantage of the present invention is that it allows the application of cold therapy without freezing;

A further advantage of the present invention is that it allows the application of magnet therapy;

A further advantage of the present invention is that it allows the application of moist heat and magnet therapy;

A further advantage of the present invention is that it allows the application of dry heat and magnet therapy;

A further advantage of the present invention is that it allows the application of cold and magnet therapy;

A further advantage of the present invention is that when applied using a combination of magnets and heat or magnets and cold it improves the therapeutic benefit of the application of magnets and/or heat and cold alone;

A further advantage of the present invention is that it provides improved nontoxic resistance to mold, mildew, and fungus or bacteria growth;

A further advantage of the present invention is that it decreases the amount of time required for hydration of the filler material;

A further advantage of the present invention is that it improves the delivery of cold therapy;

A further advantage of the present invention is that it allows the user to vary the number of magnets according to the area being treated and depth of penetration, several magnets grouped together for stronger and deeper penetration or spaced apart for a more wide spread effect;

A further advantage of the present invention is that the envelope covering the magnet has a fabric layer between the user and the magnet to protect the skin from irritation or damage due to heat transfer;

A further advantage of the present invention is that it provides an improved barrier restricting the interior filler material egress to the surface of the pack;

A further advantage of the present invention is that it eliminates any sticky or tacky feeling on the surface of the water permeable membrane by rapid dehydration of any filler material that does reach the surface of the pack.

These and other objects of the invention will be apparent to those skilled in this art from the following detailed description of a preferred embodiment of the invention.

BRIEF DESCRIPTION OF THE DRAWINGS

The invention is further described in the accompanying drawings, in which.

DETAILED DESCRIPTION OF THE PREFERRED EMBODIMENTS

Figure 1:
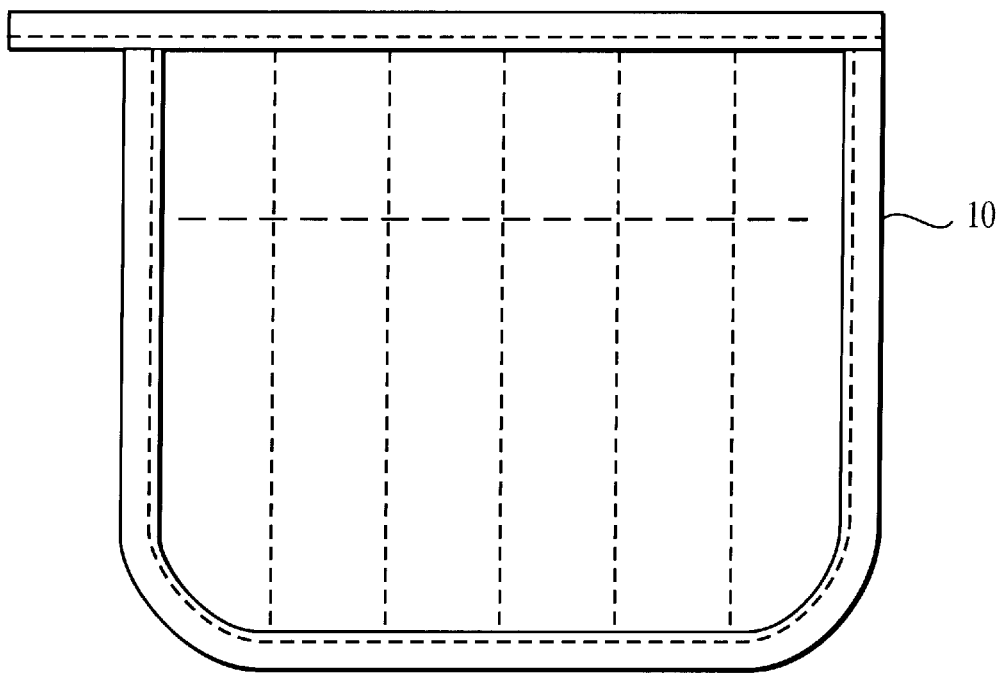
FIG. 1 is a side view of a therapeutic moist pack embodying the features of the present invention.
Figure 2:
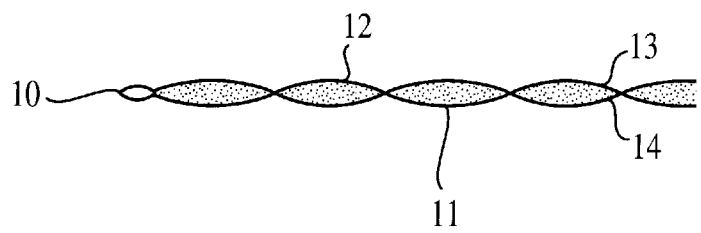
FIG. 2 is a cross-sectional view of the interior compartment containing polyacrylamide filler.

Referring to FIG. 1 the present invention provides a biomagnetic hot and cold therapy pack comprising a sealed pouch 10. FIG. 2 illustrates pouch 10 in cross-section, revealing a reconditionable water absorbent filler 11 such as polyacrylamide contained within an interior compartment 12 formed by a water permeable membrane 13 and a water impermeable membrane 14.

In an embodiment, water permeable membrane 13 is made of a composite of unbroken loop (UBL-Velcro-receptive) INTERA NYLON or INTERA polyester fabric fused or laminated to ester or polyether foam.

Figure 3:
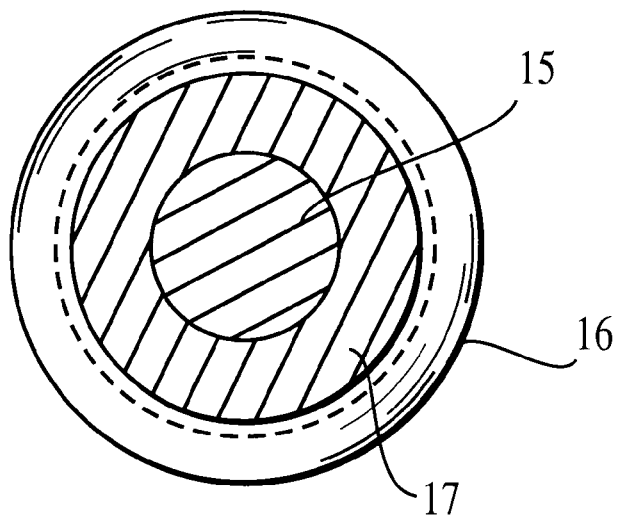
FIG. 3 is a side view of an envelope containing a magnet.
Figure 4:
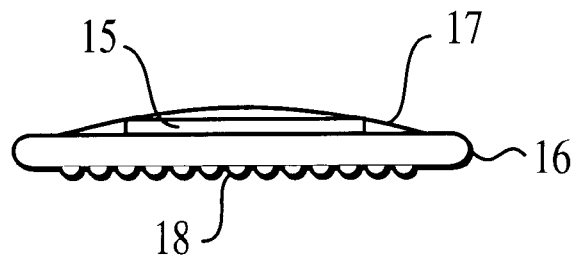
FIG. 4 is a cross-sectional view of the envelope containing a magnet.
Figure 5:
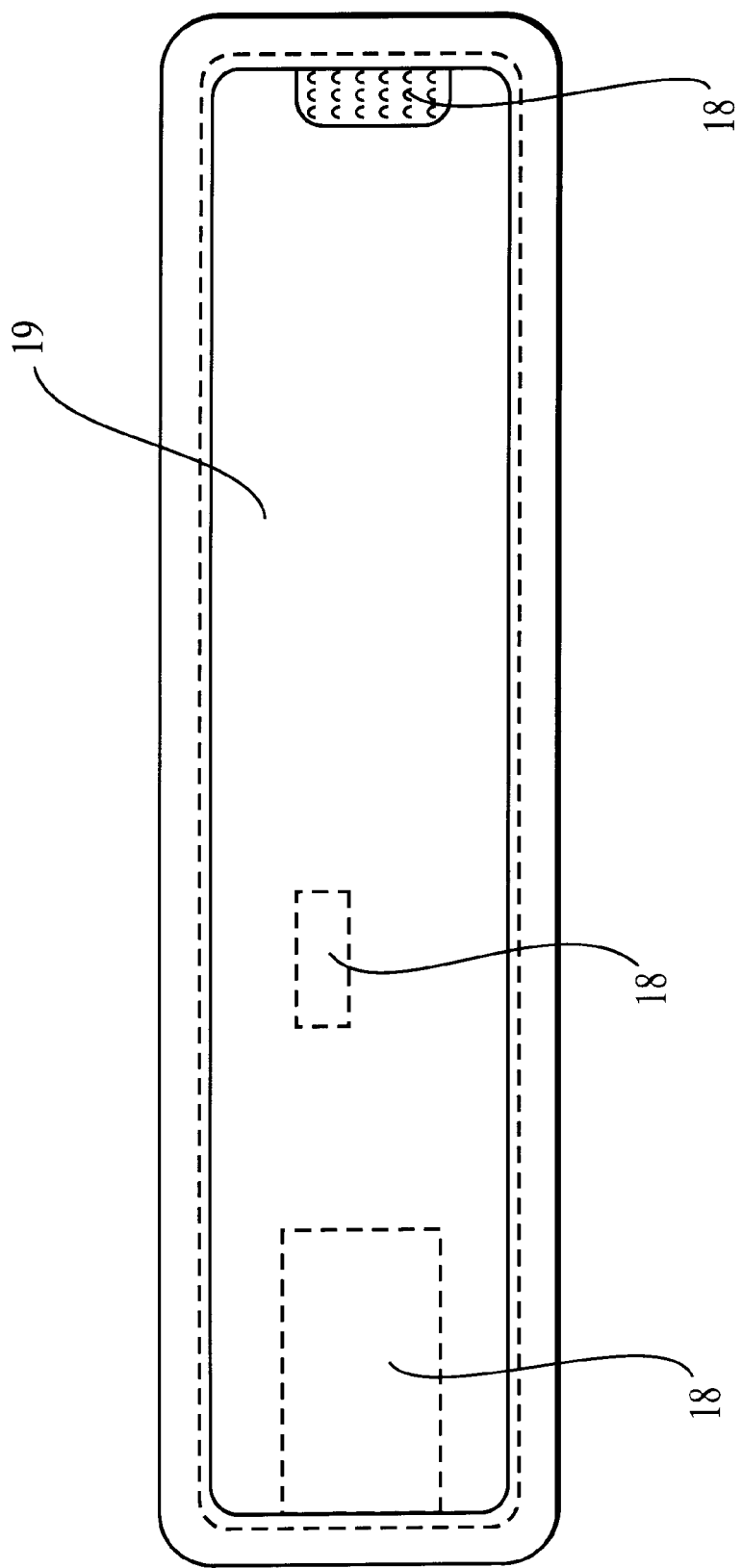
FIG. 5 illustrates the accessory strap.

Referring to FIG. 3 and FIG. 4, in an embodiment the invention provides at least one magnet 15 sealed in an envelop 16 comprising fabric ideally made of NYLON or polyester mesh 17 on one side and VELCROtype hook fabric 18 on an opposite side allowing the attachment of envelope 16 to UBL surfaces. FIG. 5 details accessory strap 19 with UBL surface on one side and Velcro-type hook fabric 18 on both ends. Accessory strap 19 is preferably made of elastic, which allows envelope 16 to be attached separately from the pack or applied from the water impermeable side of the pack. In this manner, either hot, cold or magnetic therapy, or any combination of the treatment modalities, may be utilized.

Water permeable membrane 13 delivers moist heat therapy or a combination of moist heat and magnetic therapy when a pack is hydrated by soaking in water and heated to the appropriate therapeutic temperature of 120 degrees F. and one or more envelopes 15 are arranged on the pack by means of UBL pouch surface and hook attachment surface 18 of envelope 16. Each magnet 15 is preferably made of high field strength materials capable of being magnetized to a surface strength of 500 Gauss. In the preferred embodiment, each magnet 15 is constructed of materials such as ceramic such that each may withstand being heated in a microwave to temperatures of at least 145 degrees F. and being cooled to 35 degrees F. without damage.

In the illustrated embodiment the water impermeable membrane 13 is made from vinyl or vinyl laminate, and may be treated with a mold/mildew inhibitor. The water impermeable membrane 13 delivers cold therapy when the pack is hydrated by soaking in water and cooled to the appropriate therapeutic temperature of approximately 48 degrees F. The water impermeable membrane 13 also provides dry heat therapy when the pack is hydrated by soaking in water and heated to the appropriate therapeutic temperature of approximately 120 degrees F. Magnetic therapy may be combined with either cold or heat therapy by securing envelope 16 in place against the area to be treated by an elastic strap device 19 with a UBL surface and Velcro-type hook attachment or by attaching one or more magnets to a UBL surface of water permeable membrane 13.

In an embodiment water permeable membrane 13 is made of patented hydrophilic fabric such as INTERA NYLON or INTERA polyester laminated to polyether or ester foam that promotes ingress of water into the interior compartment, but also prevents the escape of the water absorbent filler. This water permeable membrane 13 is unique in that it incorporates patented technology that greatly improves the performance of the pack. When the vinyl side of the pack is removed from the refrigerator and applied to the skin, the pack temperature is approximately 40–43 degrees F. Immediately upon application the pack begins to absorb heat from the skin. Uniquely the INTERA fabric encompassing the pouch opposite the vinyl improves the rate of evaporation, which in itself is a cooling process, thus allowing the pack to deliver the medically recommended range of cold therapy without freezing, and eliminates the possibility of frostbite or skin damage. The ability to deliver the medically recommended range of cold therapy without freezing the pack also allows much more comfortable cold therapy without the biting sting associated with packs which require freezing. Utilizing the illustrated embodiment at the conclusion of cold treatment application of the medically recommended 20 minutes, the surface of the pack is approximately 47–50 degrees F., within the preferred temperature range for cold therapy.

The present invention further provides a method of preparing a therapeutic pack comprising the steps of providing a water permeable envelope with one side having composite layers which is water permeable backed by an opposite side with a water impermeable material and defining an interior compartment, filling the interior compartment with a reconditionable water absorbent filler, and confining the reconditionable water absorbent filler in the interior compartment.

Moreover, the present invention provides a method for administering moist heat, dry heat, cold, or moist heat and magnets, dry heat and magnets, cold and magnets or magnets without heat or cold. A therapeutic pack is provided including a water permeable envelope defining an interior compartment, and reconditionable water absorbent filler. Soaking in water hydrates the water absorbent filler and the pouch may be temperature conditioned by either heating or cooling to a therapeutic temperature. Next, the pouch is applied to the area to be treated, with or without magnets, depending on the type of treatment being administered. Moist heat or moist heat and magnet therapy is applied when the water permeable side of the pouch is directed toward the area to be treated. Dry heat or cold therapy is applied when the water impermeable side of the pouch is directed toward the area to be treated. Dry heat or cold therapy combined with magnet therapy is applied when the water impermeable side of the pouch is directed toward the area to be treated and the magnetic accessory and elastic strap accessory are used to secure the envelopes containing the magnets. The vinyl side of the pouch is used for cold application as it readily transfers cold from the water activated filler material to the area to be treated, and transfers dry heat from the water activated filler material since the vinyl is not water permeable, and does not create an insulation barrier between the filler material and the area being treated. Then, after sufficient therapeutic treatment, the pouch is removed from the patient. Thereafter, the above steps may be repeated as needed for therapy.

While a preferred form of the invention has been shown in the drawings and described, since variations in the preferred form will be apparent to those skilled in the art, the invention should not be construed as limited to the specific form shown and described, but instead is as set forth in the following claims.

I claim:

1. A therapeutic magnetic hot and cold pack comprising:
  a sealed pouch having a first and a second side, said first side being water permeable and said second side being water impermeable, defining an interior compartment;

water-absorbent filler disposed within said interior compartment, said water absorbent filler being capable of retaining heat or cold for a therapeutically useful length of time;

at least one magnet positioned on said sealed pouch an accessory strap to affix said sealed pouch to the area of treatment;

a means for removably securing said magnet to said sealed pouch.

2. The therapeutic magnetic hot and cold pack of claim 1 wherein said water absorbent filler is selected from a group of super absorbent polymers such as polyacrylamide.

3. The therapeutic magnetic hot and cold pack of claim 1 wherein said first, water permeable side is a composite of unbroken loop (UBL) INTERA® polyester or INTERA®NYLON® fabric laminated or fused to a ester foam material.

4. The therapeutic magnetic hot and cold pack of claim 1 wherein said second side comprises at least 5 mm unbroken loop (UBL) laminate vinyl.

5. The therapeutic magnetic hot and cold pack of claim 1 in which said first side further comprises means to limit the egress of super absorbent polymer molecules.

6. The therapeutic magnetic hot and cold pack of claim 1 wherein said first side further comprises means to dehydrate any super absorbent polymer residue which escapes through the water permeable membrane.

7. The therapeutic magnetic hot and cold pack of claim 1 wherein said interior compartment is partitioned into a plurality of cavities.

8. The therapeutic magnetic hot and cold pack of claim 1 wherein said magnet is constructed from a group of high field strength ceramic or flexible materials capable of being magnetized to a surface strength of at least 500 Gauss.

9. The therapeutic magnetic hot and cold pack of claim 1 wherein said magnet is constructed from a group of high field strength ceramic or flexible materials and capable of being magnetized either conventionally, multi-polar or concentric configuration and sealed in an envelope made of fabric on one side and Velcro®-type hook fabric on the opposite side allowing thy attachment of envelope to unbroken loop (UBL) surfaces.

10. The therapeutic magnetic hot and cold pack of claim 1 wherein said magnet is capable of withstanding heating in a microwave oven or heated conventionally to temperatures of at least 165 degrees F. or cooled to 35 degrees F. without damage.

11. The therapeutic magnetic hot and cold pack of claim 1 wherein said accessory strap is constructed of elastic material such as neoprene and capable of securely holding said magnet and/or said pouch by means of unbroken loop (UBL) surface and Velcro®-type hook attachments such that the magnet and/or said pouch may be positioned and securely held over the area to be treated.

12. A method of preparing a therapeutic magnetic hot and cold pack comprising the steps of:

providing a pouch having a first side composed of a water permeable membrane and a second side composed of a water impermeable membrane, said first side and said second side defining an interior compartment;

filling the interior compartment with a water absorbent filler;

providing a magnet selected from a group of ceramic or flexible magnetic materials;

providing an elastic accessory strap comprised of elastic laminate material such as neoprene having an unbroken loop (UBL) surface and further having UBL hook attached to a first and a second end.

* * * * *